United States Patent [19]
Lee et al.

[11] Patent Number: 6,053,955
[45] Date of Patent: Apr. 25, 2000

[54] POLYETHER AMINO ACID ESTER COMPOUNDS, PREPARATION METHOD AND USE THEREOF

[75] Inventors: Byung Hyung Lee; Woo Sun Kim; Sang Chul Lim; Ho Young Kwon; Dae Joon Yang, all of Taejon, Rep. of Korea

[73] Assignee: SK Corporation, Seoul, Rep. of Korea

[21] Appl. No.: 09/155,415

[22] PCT Filed: Apr. 1, 1997

[86] PCT No.: PCT/KR97/00056

§ 371 Date: Sep. 25, 1998

§ 102(e) Date: Sep. 25, 1998

[87] PCT Pub. No.: WO97/36854

PCT Pub. Date: Oct. 9, 1997

[30] Foreign Application Priority Data

Apr. 1, 1996 [KR] Rep. of Korea ............. 96/10307

[51] Int. Cl.[7] .................. C10L 1/18; C10L 1/22
[52] U.S. Cl. ............... 44/391; 44/410; 560/169; 560/193; 560/198
[58] Field of Search ............. 44/391, 410; 560/169, 560/193, 198

[56] References Cited

U.S. PATENT DOCUMENTS 5,468,263  11/1995  Chung et al. ................ 44/391

*Primary Examiner*—Jacqueline V. Howard
*Assistant Examiner*—Cephia D. Toomer
*Attorney, Agent, or Firm*—Abelman, Frayne & Schwab

[57] ABSTRACT

The present invention relates to polyether amino acid ester compounds, preparation method and their use as hydrocarbon fuel additives.

22 Claims, No Drawings

POLYETHER AMINO ACID ESTER COMPOUNDS, PREPARATION METHOD AND USE THEREOF

This application is a 371 of PCT/KR97/00056 filed, Apr. 1, 1997.

TECHNICAL FIELD

The present invention relates to polyether amino acid ester compounds, preparation method and use thereof. More particularly, the present invention relates to polyether amino acid ester compounds represented by the following formula (I):

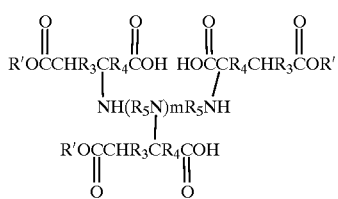

wherein R' is a radical of the alkylphenylpoly(oxyalkylene) alcohol represented by the following formula (II);

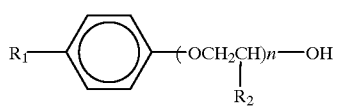

wherein n is an integer of 5 to 50, $R_1$ is a linear or branched alkyl group containing from 4 to 25 carbon atoms and $R_2$ is an alkyl group containing from 1 to 3 carbon atoms;

$R_3$ and $R_4$, which may be the same or different, each represent H or an alkyl group containing from 1 to 3 carbon atoms;

$R_5$ represents a linear or branched alkyl group containing from 2 to 6 carbon atoms; and m is 0 or an integer between 1 and 6.

The polyether amino acid ester compound of formula (I) can act to remove deposits generated in the combustion chamber and intake lines of an automobile during its fuel combustion when the engine is operated or to prevent deposits from being produced, thereby showing a significant improvement in traveling ability, fuel-to-distance ratio and reduction in exhaust gas pollution.

The present invention relates to a method for preparing the polyether amino acid ester compounds, represented by the above formula (I). Also, the present invention is concerned with use of the polyether amino acid ester compound represented by the above formula (I) for a fuel detergent. The present invention is also concerned with a diluted fuel detergent solution and fuel compositions containing the polyether amino acid ester compounds represented by the above formula (I) as a fuel detergent.

BACKGROUND ART

Imperfect combustion of hydrocarbon fuel for automobiles causes carbon materials to be formed or deposited on many sites within the engine of automobiles. These carbon deposits within the engine combustion chamber have a deleterious influence on the engine. For example, the carbon deposits within the combustion chamber reduce its space, so that, when a fuel-air mixture is compressed, a compression ratio higher than a designed one is obtained, causing a knocking phenomenon. Protracted engine-knocking gives stress fatigue or abrasion to main parts of the engine, resulting in increasing the maintenance cost of automobiles and reducing its life span.

Also, it is known that, when idling or driving an automobile at low speeds, the carbon deposits formed within its engine interrupt the flow of air so that a overfull-air mixture is injected into the engine. The mixture is imperfectly burned, to make the engine idle roughly and to exhaust excess hydrocarbons and carbon monoxide.

U.S. Pat. No. 4,881,945 discloses that alkylphenyl poly (oxyalkylene)amino carbamate is effective for controlling the amount of fuel deposits. According to this patent, alkylphenyl poly(oxyalkylene)alcohol is reacted to phosgene to synthesize an intermediate of chloroformate which is, then, reacted to polyamine, to give a desired alkylphenylpoly(oxyakylene) aminocarbamate. However, extreme care must be taken of phosgene gas because it is highly toxic. Further, the phosgene gas left unreacted in the reaction and the hydrochloride gas produced during the reaction must be removed, which makes the production process more complicated.

According to many patents including the above-cited patent and U.S. Pat Nos. 4,160,648, 4,243,798, 4,191,537 and 4,197,409, polyamine is used at 15-fold equivalents relative to chloroformate, the intermediate, to produce a desirable monoaminocarbamates, which are used as an additive for controlling fuel deposits. The excess polyamine used must be removed by washing with distilled water after the reaction. This is economically unfavorable because polyamine is unnecessarily consumed or a further process is required to reclaim the excess polyamine in addition to the washing process.

When polyamine is reacted with chloroformate, polyamine hydrochloride is produced at the same moles with aminocarbamates, the desired product. The chloride salt thus produced is unfavorable to the fuel oil and may be a cause of corrosion and plugging up the engine. Accordingly, the problematic compound must be reduced into a very low level or completely removed.

U.S. Pat. No. 5,468,263 to Chung et al., which is assigned to Yukong Limited, discloses that an alkylphenyl poly (oxyalkylene)polyamine acid ester compound as a fuel detergent is prepared by reacting alkylphenyl poly (oxyalkylene)maleate derivate compound with polyamine at an equivalent ratio of 0.5:1 to 1:20. The excess polyamine used must be removed and this is economically unfavorable because polyamine is unnecessarily consumed or a further process is required to reclaim the excess polyamine. Furthermore, the polyamine left unreacted in the reaction affects adversely the storage stability of the final products, for example, when storing in an oven maintained at 54° C. for one month, a deposit is generated in an average amount of 0.1 to 0.2 wt % and the detergent becomes turbid.

DISCLOSURE OF THE INVENTION

The intensive and thorough research of the present inventors for solving the above problems encountered in prior arts results in the development of a novel compound superior in cleaning carbon deposits formed in automobile engines and a method for the preparing the same. The reaction pathway through an alkyl phenylpoly(oxyalkylene) maleate intermediate avoids the use of toxic phosgene gas unreacted in the chloroformate intermediate pathway and hydrochloride gas causing the corrosion or plugging of equipment, allowing industrial production scale. In addition, the intermediate of the present invention forms a dimer or oligomer by the reaction with a polyamine, whose chemical structure is superior in thermal stability, so that the dimeric or oligomeric product can play its cleaning role in various parts of engine. On the other hand, since the detergent itself is thermally decomposed very well within the combustion chamber of the engine, little residue exists therein.

Therefore, it is an object of the present invention to provide a novel polyether amino acid ester compound which has an excellent cleaning ability for fuel oil without deleteriously affecting the increase for octane value.

It is another objective of the present invention to provide a method for preparing the novel polyether amino ester compound.

It is a further object of the present invention to provide a fuel detergent comprising the novel polyether amino ester compound as an active gradient.

It is still another object of the present invention to provide a diluted fuel detergent solution comprising the fuel detergent.

It is still a further object of the present invention to provide a hydrocarbon fuel composition comprising either the fuel detergent or the diluted fuel detergent solution.

In accordance with an aspect of the present invention, there is provided a polyether amino acid ester compound, represented by the following formula (I):

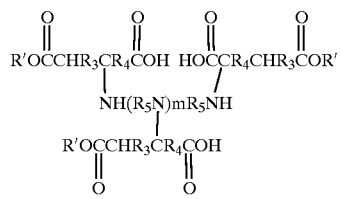

(I)

wherein R' is a radical of the alkylphenylpoly(oxyalkylene) alcohol represented by the following formula (II);

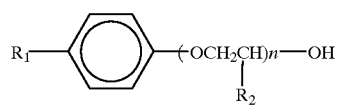

(II)

wherein n is an integer of 5 to 50, preferably an integer of 10 to 30; $R_1$ is a linear or branched alkyl group containing 4 to 25 carbon atoms, preferably from 5 to 20 carbon atoms; and $R_2$ is an alkyl group containing from 1 to 3 carbon atoms, preferably an alkyl group containing from 1 to 2 carbon atoms;

$R_3$ and $R_4$, which may be the same or ~ from 1 to 3 carbon atoms, preferably H or an alkyl containing from 1 to 2 carbon atoms;

$R_5$ represents ~ from 2 to 6 carbon atoms, preferably a linear or branched alkyl group containing from 2 to 3 carbon atoms; and m is 0 or an integer between 1 and 6, preferably of 1 to 4.

In accordance with another aspect of the present invention, there is provided a method for preparing a polyether amino acid ester compound represented by the formula (I), which comprises reacting an alkylphenyl poly(oxyalkylene)alcohol represented by the formula (II) with a maleic acid derivative represented by the formula (III) or a maleic anhydride derivative represented by the formula (III') at an equivalent ratio of 1:1 to 1:5 in the presence or absence of a catalyst in an inert organic solvent, to give an alkylphenylpoly(oxyalkylene) maleate represented by the formula (IV), and reacting it with a polyamine represented by the formula (V) at an equivalent ratio of 2:1 to 5:1.

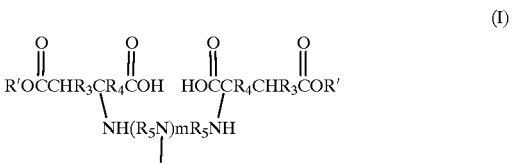

(I)

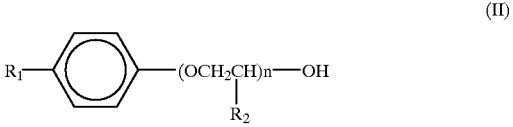

(II)

(III)

(III')

(IV)

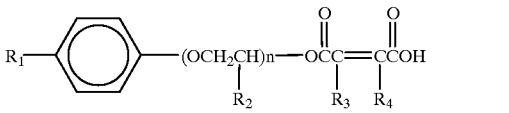

$H_2N(R_5NH)mR_5NH_2$ (V)

wherein, R', $R_1$, $R_2$, $R_3$, $R_4$, $R_5$, m and n each are as defined above.

In accordance with a further aspect of the present invention, there is provided a diluted fuel detergent solution, comprising the compound of the formula (I) as a fuel detergent at an amount of 5 to 80% by weight and an organic solvent having a boiling point of from about 100 to about 200° C.

In accordance with still a further aspect of the present invention, there is provided a hydrocarbon fuel composition, comprising either the compound of the formula (I) or the diluted fuel detergent solution at an amount of 2.5 to 4,000 ppm and at an amount of 50 to 5,000 ppm, respectively, in a hydrocarbon fuel.

BEST MODE FOR CARRYING OUT THE INVENTION

According to the present invention, a polyether amino acid ester compound represented by the following formula (I) is obtained by reacting an alkylphenylpoly(oxyalkylene) alcohol represented by the following formula (II) with a maleic acid derivative represented by the following formula (III) or a maleic anhydride represented by the following formula (III') to give an alkylphenyl poly(oxyalkylene) maleate represented by the following formula (IV), followed by reacting it with a polyamine represented by the following formula (V):

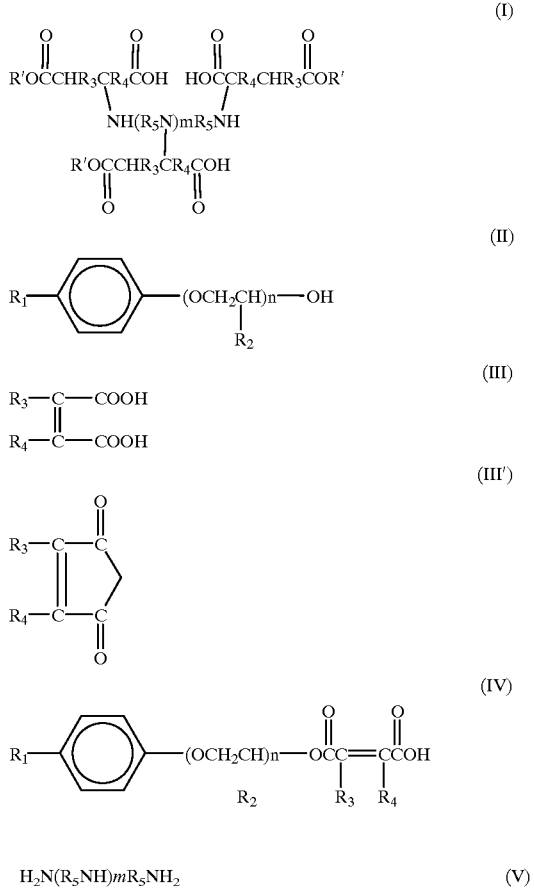

$H_2N(R_5NH)mR_5NH_2$ (V)

wherein, R', $R_1$, $R_2$, $R_3$, $R_4$, $R_5$, m and n each are as defined, above. For example, an alkylphenylpoly(oxyalkylene) alcohol of formula (II), which can be obtained by reacting alkyl phenol with alkylene oxide, such as propylene oxide, butylene oxide and pentylene oxide, is reacted with a maleic acid derivative or its anhydride of formula (III) or (III') in the presence or absence of a catalyst, to give an alkylphenylpoly (oxyalkylene)maleate of formula (IV) which is, then, reacted to polyamine of formula (V) to produce a compound of formula (I) superior in cleaning property.

The alkylphenylpoly(oxyalkylene)maleate, represented by formula (IV), is an intermediate which links the alkylphenyl poly(oxyalkylene)alcohol, represented by formula (II), useful in preparing a fuel detergent of the present invention, to the polyamine, represented by formula (V). The intermediate can be obtained by reacting the alkylphenylpoly(oxyalkylene)alcohol with the maleic acid derivative or its anhydride at an equivalent ratio of 1:1 to 1:5 and preferably 1:1 to 1:2 and at a temperature of 10 to 200° C. for 1 to 10 hours with stirring in the presence or absence of a catalyst.

Examples of inert solvents useful for the reaction include hydrocarbon solvents, such as hexane, cyclohexane, benzene, toluene, xylene and those commercially available such as that sold by YuKong Ltd., Korea, identified as "KOCOSOL 100"a mixed aromatic solvent containing $C_7$ or higher, and mixtures thereof with preference to xylene.

In order to accelerate the reaction, a catalyst may be used, such as triethylamine, para-toluene sulfonic acid, dibutyl tin oxide and titanium iso-peroxide. For example, triethyl amine is used at an amount of 0.01 to 1 equivalent relative to maleic anhydride and preferably 0.1 to 0.5 equivalent.

The maleic acid derivative or its anhydride useful in the present invention includes maleic anhydride, 2,3-dimethyl maleic anhydride, 2-methyl maleic anhydride, 2-ethyl maleic anhydride, maleic acid, 2,3-dimethyl maleic acid, 2-methyl maleic acid and 2-ethyl maleic acid and more preferably maleic anhydride.

When the alkylphenylpoly(oxyalkylene)maleate derivative of formula (IV) is reacted with the polyamine of formula (V) to produce the desired compound of formula (I), the equivalent ratio of the alkylphenylpoly (oxyalkylene) maleate derivative to the polyamine can be controlled within the range of 2:1 to 5:1, depending on the amine content in the polyamine and preferably 2;1 to 3:1. The reaction is carried out at a temperature of 5 to 100° C. and preferably 20 to 60° C. for a period of 1 to 20 hours and preferably 1 to 5 hours.

Useful polyamines in the present invention include ethylene diamine, substituted polyamines and polyalkylene polyamine, all of which are referred to as "polyamines" hereinafter and preferably exemplified by ethylene diamine, diethylene triamine, triethylene tetramine, tetraethylene pentamine, 1,2-propylene diamine, di-(1,2-propylene) triamine, di-(1,3-propylene)triamine, N,N-dimethyl-1,3-diaminopropane,N,N-di-(2-hydroxyethyl)-1,3-propylenediamine.

On preparing the objective compounds of the present invention, if the nitrogen atoms are not geometrically identical, various substituted isomers may exist. Therefore, they are also within the objective compounds of the present invention.

The present invention pertains to a diluted fuel detergent solution containing the fuel detergent represented by formula (I), which comprises the compound of formula (I) at an amount of 5 to 80% by weight and preferably 30 to 50% by weight and an inert organic solvent having a boiling point ranging from 100 to 200° C. The inert organic solvent includes benzene, toluene, xylene and "Kocosol 100" and aromatic solvents having boiling points higher than those of them with more preference to "Kocosol 100".

The fuel detergent of the present invention is used for a hydrocarbon fuel having a boiling point ranging from 50 to 280° C., such as gasoline, diesel and the like. The dosage amount of the fuel detergent or its diluted solution thus prepared depends on the types of fuel and additives contained therein and on whether other additives are present or not. Usually, the fuel detergent is used at an amount of 2.5 to 4,000 ppm and preferably 5 to 1,600 ppm while the diluted fuel detergent solution at an amount, of 50 to 5,000 ppm and preferably 100 to 2,000 ppm. Higher concentration, for example, 2,000 to 5,000 ppm of the diluted fuel detergent solution shows the clean-up property that carbon deposits formed in the intake system of automobile engine are removed. Of course, the fuel detergent of the present invention can be used for a fuel containing other additives of different types, such as surfactant, antioxidant and anti-knocking agent.

The preparation method of the novel compound, the use thereof as a fuel detergent, and the performance and effect of the diluted fuel detergent solution comprising the novel compound will be described in detail through the following examples which are set forth to illustrate, but are not to be construed as the limit of the present invention.

EXAMPLE I

Preparation of Tetrapropenylphenylpoly(oxybutylene) maleate 48 g of tetrapropenylphenylpoly(oxybutylene)alcohol (average molecular weight=1,600) was dissolved in 50 ml of xylene and the resulting solution was poured in a 250 ml three-neck bottom-round flask equipped with a thermometer, a condenser and a dropping funnel. 3 g of maleic anhydride was added in the reactor and dissolved by stirring at room temperature for 30 min.

Following complete dissolution, the resulting solution was heated up to 80° C. 2 ml of triethylamine, as a base catalyst, was diluted to 10-folds in xylene and slowly added to the solution for 1 hour with the aid of an injection pump. Reaction was conducted for 8 hours in the reaction system which was maintained at 90° C. Thin layer chromatography was used to detect the completion of the reaction. Thereafter, the reactor was cooled.

The resulting reaction mixture was washed with 100 ml of distilled water to remove unreacted maleic anhydride and the catalyst, triethylamine, and an organic phase of xylene was obtained in which the desired compound was dissolved.

The organic phase was dehydrated by adding magnesium sulfate and filtered through a filter funnel to give a clear solution of pale yellow. The solvent was removed by distillation under vacuum to obtain 46 g of the title compound of pale yellow liquid.

The product showed characteristic peak at 1,732 cm$^{-1}$ by Fourier transform infrared (FT-IR).

EXAMPLE II

Preparation of Tetrapropenylphenylpoly(oxypropylene) maleate 42.6 g of tetrapropenylphenylpoly(oxypropylene) alcohol (average molecular weight=1,420) was dissolved in 50 ml of xylene and the resulting solution was poured in a 250 ml three-neck round bottom flask. 3 g of maleic anhydride was added in the reactor and dissolved by stirring at room temperature for 30 min.

Following complete dissolution, the resulting solution was heated up to 80° C. 2 ml of triethylamine, as a base catalyst, was diluted to 10-folds in xylene and slowly added to the reaction solution for 1 hour with the aid of an injection pump. Reaction was made for 8 hours in the reaction system which was maintained at 90° C. Thin layer chromatography was used to detect the completion of the reaction. Thereafter, the reactor was cooled.

The resulting reaction mixture was washed with 100 ml of distilled water to remove unreacted maleic anhydride and the catalyst, triethylamine, and an organic phase of xylene was obtained in which the desired compound was dissolved.

Magnesium sulfate was added to remove water and a clear solution of pale yellow was obtained by filtration through a filter funnel. The solvent was removed by distillation under vacuum to produce 42 g of the title compound of pale yellow liquid.

The product showed characteristic peak at 1,732 cm$^{-1}$ by Fourier transform infrared (FT-IR).

EXAMPLE III

Reaction of Tetrapropenylphenylpoly(oxybutylene)maleate with Diethylenetriamine in 2:1 equivalent ratio 46 g of the tetrapropenylphenylpoly(oxybutylene) maleate obtained in Example I was diluted with 50 ml of xylene in a 250 ml three-neck bottom round flask equipped with a thermometer, a condenser and a dropping funnel. 1.4 g of diethylenetriamine was dissolved in 10 ml of xylene and added into the reactor with the dropping funnel. Thereafter, reaction was proceeded for 2 hours at room temperature. After being detected for reaction termination as measured by thin layer chromatography, the reaction solution was condensed under vacuum to give 45 g of a pale yellow liquid containing a desired compound.

A product showed chracteristic peaks at 1,730 cm$^{-1}$, 1,648 cm$^{-1}$ and 1,506 cm$^{-1}$ by FT-IR. The average molecular weight of the product was found to be 3,470 as measured by GPC.

EXAMPLE IV

Reaction of Tetrapropenylphenylpoly(oxypropylene) maleate with Diethylenetriamine in 2:1 equivalent ratio 46 g of the tetrapropenylphenylpoly(oxypropylene) maleate obtained in Example II was diluted with 50 ml of xylene in a 250 ml three-neck bottom round flask equipped with a thermometer, a condenser and a dropping funnel. 1.43 g of diethylenetriamine was dissolved in 10 ml of xylene and added into the reactor with the dropping funnel. Thereafter, reaction was proceeded for 2 hours at room temperature. After being detected for reaction termination as measured by thin layer chromatography, the reaction solution was condensed under vacuum to give 43 g of a pale yellow liquid containing a desired compound.

The product showed chracteristic peaks at 1,730 cm$^{-1}$, 1,648 cm$^{-1}$ and 1,506 cm$^{-1}$ by FT-IR. The average molecular weight of the product was found to be 3,135 as measured by GPC.

EXAMPLE V

Reaction of Tetrapropenylphenylpoly(oxybutylene)maleate with Triethylenetetramine in 2:1 equivalent ratio 46 g of the tetrapropenylphenylpoly(oxybutylene) maleate obtained in Example I was diluted with 50 ml of xylene in a 250 ml three-neck bottom round flask equipped with a thermometer, a condenser and a dropping funnel. 2.0 g of triethylenetetramine was dissolved in 10 ml of xylene and added into the reactor with the aid of the dropping funnel. Thereafter, reaction was proceeded for 2 hours at room temperature. After being detected for reaction termination as measured by thin layer chromatography, the reaction solution was condensed under vacuum to give 45 g of a desired compound.

The product showed characteristic peaks at 1,648 cm$^{-1}$ and 1,506 cm$^{-1}$ on FT-IR. The average molecular weight of the product was found to be 3,530 as measured by GPC.

EXAMPLE VI

Reaction of Tetrapropenylphenylpoly(oxybutylene)maleate with Diethylenetriamine in 3:1 equivalent ratio The procedure of Example III was repeated except that the equivalent ratio of tetrapropenylphenylpoly (oxybutylene)maleate to diethylenetriamine was 3:1.

EXAMPLE VII

Reaction of Tetrapropenylphenylpoly(oxybutylene)maleate to Triethylenetetramine in 3:1 equivalent ratio The procedure of Example V was repeated except that the equivalent ratio of tetrapropenylphenylpoly (oxybutylene) maleate to triethylenetetramine was 3:1.

EXAMPLE VIII

Preparation of a diluted fuel detergent solution

Each of the products obtained in Examples III, IV, V, VI and VII was mixed with as much as Kocosol 100, an aromatic solvent, to produce a 50% diluted fuel detergent solution.

EXAMPLE IX

Bench Test of Fuel Detergent (ISD TEST)

Each of the diluted solution produced in Example VIII was added at 100 ppm and 200 ppm to the gasoline which did not contain any detergents and the resulting gasoline was tested using an ISD tester, which was developed by Southwest Research Institute (SwRI), USA.

Aluminum test bar was fixed on the tester and one liter of the fuel to be tested was prepared. After the test bar was heated up to 200° C. under the control of a heater, the fuel was injected through a fuel pump into the test bar for 7 hours. Then, the temperature controller of the heater was set to zero Celsius to cool the test bar. After being cooled to room temperature, the test bar was removed from the tester, washed with hexane, dried for 15 min. in an oven maintained at 100° C., and stored in a desiccator until it was cooled to room temperature. The test bar was weighed for calculating the difference in weight between pre-test and post-test, which reflected the fuel deposit. The results are given as shown in Table 1 below.

TABLE 1

|  | Deposit Amount (mg) | |
| --- | --- | --- |
| Additive | 100 ppm | 200 ppm |
| No additive | 5.3 | |
| Exmp.III 50% diluted soln. | 0.5 | 0.35 |
| Exmp.IV 50% diluted soln. | 1.25 | 0.80 |
| Exmp.V 50% diluted soln. | 0.54 | 0.45 |
| Exmp.VI 50% diluted soln. | 0.7 | 0.6 |
| Exmp.VII 50% diluted soln. | 0.75 | 0.58 |
| PIBIS diluted soln.* | 0.9 | 0.6 |

*Polyisobutylene succinimide: sold by T company.

As apparent from Table 1, the diluted solution prepared according to the present invention have a significant improvement in reducing the fuel deposit. In particular, the diluted solution of Examples III and V prevent the formation of fuel deposit with a reduction rate of 90% or more relative to no detergent addition, in both cases of 100 ppm and 200 ppm.

EXAMPLE X

Detergency Test in Engine Intake Valve

The fuel composition comprising the 50% diluted fuel detergent solution of Examples III and V was tested for cleaning an engine intake valve. The tested engine was "Elantra Engine 1.6 L DOHC" manufactured by Hyundai Motor Co., Korea, in 1991, whose performance is given as shown in Table 2 below.

TABLE 2

| Engine type | DOHC 4-cylinder |
| --- | --- |
| Power Max. | 126/6000 (PS/rpm) |
| Bore/Stroke | 82.3 × 75 mm |
| Torque Max. | 15.3/5000 (kg/rpm) |
| Displacement | 2,596 cc |
| Fuel Inject. | MPI |
| Compression Ratio | 9.2 |
| Speed Max. | 180 km/hr |

As a test mode, Benz M102E mode was employed under the test condition of Table 3 below.

TABLE 3

| Test Period | 60 hr |
| --- | --- |
| Torque | 3.1–3.7 Nm |
| Oil Temp. | 95 to 100° C. |
| Cycle | 4.5 min (800 times repeat) |
| Coolant Temp. | 90 to 95° C. |
| rpm | 800 to 3000 |
| Gear Transmission | 4 stages |
| Intake air temp. | 35 ± 2° C. |

For measuring the amount of the deposit in the intake valve, it was disassembled prior to the test and the assemblies were washed with hexane, dried, weighed in $10^{-1}$ mg scale, and assembled into the valve. Following completion of the test, the valve was again disassembled and the precipitate on the bottom of the valve was removed. The valve was washed with hexane until the finally used washing solution was clear. The washed valve was dried in an oven and weighed. The difference in weight between pre-test and post-test was considered as the deposit amount.

The diluted fuel detergent solution of the present invention was added at an amount of 200 ppm and 400 ppm and investigated for the formation of the deposit. The results are given as shown in Table 4 below.

TABLE 4

| Deposit formed depending on Amount of Additive (Unit:mg) | | |
| --- | --- | --- |
|  | Deposit Amount (mg) | |
| Additive | 200 ppm | 400 ppm |
| No additive | 175 | |
| Exmp.III 50% diluted soln. | 31.5 | 7.5 |
| Exmp.V 50% diluted soln. | 33.0 | 12.5 |
| Polyether amino acid ester** | 39.1 | 24.1 |
| PIBIS diluted soln.* | 56.7 | 35.2 |

*Polyisobutylene succinimide: sold by T company.
**Fuel detergent disclosed in U.S. Pat. No. 5,468,263.

As demonstrated from Table 4, the diluted fuel detergent solution containing the product of Example III obtained from the reaction of the tetrapropenylphenylpoly(oxybutylene)maleate with diethylenetriamine, when added at an amount of 200 ppm and 400 ppm, allowed the deposit to be formed at an amount of 31.5 mg and 7.5 mg only, respectively, which show reduction effects of 82% and 95% each, compared with 175 mg in case of no detergent.

EXAMPLE XI

Thermal Gravity Analysis (TGA)

In order to know whether the fuel detergent itself would increase the deposit within a combustion chamber, the thermal decomposition rate of the detergent was measured using a thermal gravity analyzer. This test, developed by Chevron, USA, is disclosed in U.S. Pat. No. 5,383,942, teaching that a material is heated at a rapid elevation rate under air flow and then, its volatility is measured at a temperature of 200° C. and 295° C.

In this Example, the fuel detergent of the present invention were heated to 200° C. and maintained at this temperature for 30 min. Re-heating was made for the samples until the temperature reached 295° C. which was, then, maintained for 30 min. Prior to heating, the samples each weighed about 20 mg. The weights of the materials were measured at 200° C. and 295° C. The differences in weight between at pre-heating and at 20° C. and between at 200° C and at 295° C. were recorded for calculation of their volatility. Upon heating, air was let to flow at a rate of 60 cc/min.

The analysis results of the fuel detergent of Examples III and V are given in Table 5 below, together with those of the detergent of "T" company.

TABLE 5

| Additive | Volatility (%) | | Remnant (wt %) |
|---|---|---|---|
|  | 200° C. | 295° C. | 295° C. |
| Exmp.III detergent | 12 | 97 | 3.54 |
| Exmp.V detergent | 10 | 95 | 4.26 |
| PIBIS detergent* | 8 | 64 | 29.43 |

*Polyisobutylene succinimide: sold by T company.

According to the results of Table 5, 95 to 97% of the fuel detergent of the present invention thermally decomposed and volatilized, showing that only a trace of the novel detergent are left in the combustion chamber under practical driving conditions and they have virtually little influence on the formation of deposition therein.

INDUSTRIAL APPLICABILITY

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A polyether amino acid ester compound, represented by the following formula (I):

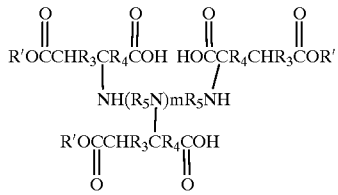

wherein R' is a radical of the alkylphenylpoly(oxyalkylene) alcohol represented by the following formula (II);

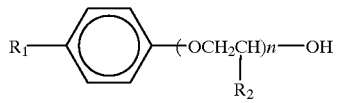

wherein n is an integer of 5 to 50, $R_1$ is a linear or branched alkyl group containing from 4 to 25 carbon atoms and $R_2$ is an alkyl group containing from 1 to 3 carbon atoms;

$R_3$ and $R_4$, which may be the same or different, each represent H or an alkyl group containing from 1 to 3 carbon atoms;

$R_5$ represents a linear or branched alkyl group containing from 2 to 6 carbon atoms; and m is 0 or an integer between 1 and 6.

2. The polyether amino acid ester compound in accordance with claim 1, wherein said $R_1$ is a linear or branched alkyl group containing 5 to 20 carbon atoms.

3. The polyether amino acid ester compound in accordance with claim 1, wherein said $R_2$ is an alkyl containing 1 to 2 carbon atoms.

4. The polyether amino acid ester compound in accordance with claim 1, wherein each $R_3$ is the same or different and is H or an alkyl containing 1 to 2 carbon atoms.

5. The polyether amino acid ester compound in accordance with claim 1, wherein said $R_4$ is same or different and is H or an alkyl containing 1 to 2 carbon atoms.

6. The polyether amino acid ester compound in accordance with claim 1, wherein said $R_5$ is a linear or branched alkyl group containing 2 to 3 carbon atoms.

7. The polyether amino acid ester compound in accordance with claim 1, wherein said m is 0 or an integer of 1 to 4.

8. The polyether amino acid ester compound in accordance with claim 1, wherein said n is an integer of 10 to 30.

9. A method for preparing a polyether amino acid ester compound represented by the following formula (I), which comprises reacting an alkylphenylpoly(oxyalkylene)alcohol represented by the following formula (II) with a maleic acid derivative represented by the following formula (III) or a maleic anhydride derivative represented by the following formula (III') at an equivalent ratio of 1:1 to 1:5 in the presence or absence of a catalyst in an inert organic solvent, to give an alkylphenylpoly(oxyalkylene) maleate represented by the following formula (IV), and reacting it with a polyamine represented by the following formula (V) at an equivalent ratio of 2:1 to 5:1:

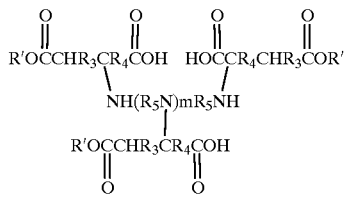

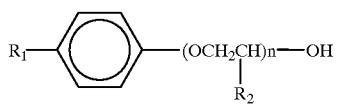

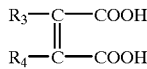

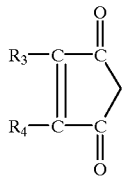

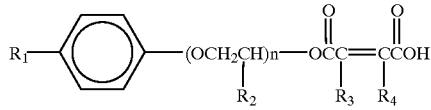

wherein,

R' is a radical of the alkylphenylpoly(oxyalkylene)alcohol represented by the formula (II);

$R_1$ is a linear or branched alkyl group containing 4 to 25 carbon atoms;

$R_2$ is an alkyl group containing 1 to 3 carbon atoms;

$R_3$ and $R_4$, which may be the same or different, each represent an alkyl group containing 1 to 3 carbon atoms;

$R_5$ represents a linear or branched alkyl group containing 2 to 6 carbon atoms;

m is 0 or an integer of 1 to 6; and n is an integer of 5 to 50.

10. The method in accordance with claim 9, wherein the reaction of said alkylphenylpoly(oxyalkylene)alcohol of formula (II) with said maleic acid derivative of formula (III) or said maleic anhydride derivative of formula (III') is carried out at a temperature of 10 to 200° C. for 1 to 10 hours with stirring.

11. The method in accordance with claim 9, wherein said inert organic solvent is selected from the group consisting of hexane, cyclohexane, benzene, toluene, xylene, a mixed aromatic solvent containing $C_7$ or higher and the mixtures thereof.

12. The method in accordance with claim 9, wherein said catalyst is selected from the group consisting of triethylamine, para-toluene sulfonic acid, dibutyltin oxide and titanium iso-peroxide and is used at an amount of 0.01 to 1 equivalent based on the equivalent of said maleic anhydride.

13. The method in accordance with claim 9, wherein the reaction of said alkylphenylpoly(oxyalkylene)maleate of formula (IV) with said polyamine of formula (V) is carried out at a temperature of 5 to 100° C. for 1 to 20 hours.

14. A diluted fuel detergent solution, comprising the compound of claim 1 as a fuel detergent at an amount of 5 to 80% by weight and an organic solvent having a boiling point of 100 to 200° C.

15. The diluted fuel detergent solution in accordance with claim 14, wherein said organic solvent is selected from the group consisting of benzene, toluene, xylene and a mixed aromatic solvent containing $C_7$ or higher.

16. A hydrocarbon fuel composition, comprising a compound of claim 1 as a fuel detergent at an amount of 2.5 to 4,000 ppm and a hydrocarbon fuel.

17. The hydrocarbon fuel composition in accordance with claim 16, wherein said hydrocarbon fuel has a boiling point ranging from 50 to 280° C.

18. The hydrocarbon fuel composition in accordance with claim 16, wherein said fuel detergent is comprised at an amount of 5 to 1,600 ppm.

19. A hydrocarbon fuel composition, comprising a diluted fuel detergent solution as claimed in claim 14 at an amount of 50 to 5,000 ppm and a hydrocarbon fuel.

20. The hydrocarbon fuel composition in accordance with claim 19, wherein said hydrocarbon fuel has a boiling point ranging from 50 to 280° C.

21. The hydrocarbon fuel composition in accordance with claim 19, wherein said diluted fuel detergent solution is comprised at an amount of 100 to 2,000 ppm.

22. A process for the cleaning of a fuel oil, which comprises:

adding a compound in accordance with Formula (I)

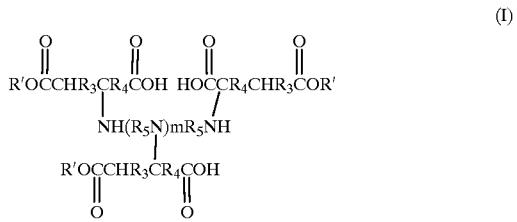

(I)

to the fuel oil, wherein R' is a radical of the alkylphenylpoly(oxyalkylene)alcohol represented by the following formula (II);

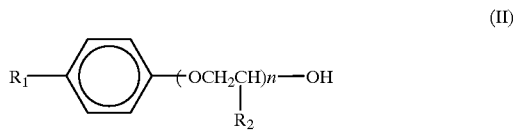

(II)

wherein n is an integer of 5 to 50, $R_1$ is a linear or branched alkyl group containing from 4 to 25 carbon atoms and $R_2$ is an alkyl group containing from 1 to 3 carbon atoms;

$R_3$ and $R_4$, which may be the same or different, each represent H or an alkyl group containing from 1 to 3 carbon atoms;

$R_5$ represents a linear or branched alkyl group containing from 2 to 6 carbon atoms; and m is 0 or an integer between 1 and 6.

* * * * *